United States Patent
Russo et al.

(10) Patent No.: US 11,890,027 B2
(45) Date of Patent: Feb. 6, 2024

(54) MICROFORCEPS

(71) Applicant: United States Endoscopy Group, Inc., Mentor, OH (US)

(72) Inventors: Jessica Russo, Sagamore Hills, OH (US); Keith R. John, Chardon, OH (US); Alex Uspenski, Chardon, OH (US); Gerald Chiappone, Painesville, OH (US)

(73) Assignee: UNITED STATES ENDOSCOPY GROUP, INC., Mentor, OH (US)

( * ) Notice: Subject to any disclaimer, the term of this patent is extended or adjusted under 35 U.S.C. 154(b) by 0 days.

(21) Appl. No.: 17/124,932

(22) Filed: Dec. 17, 2020

(65) Prior Publication Data
US 2021/0186545 A1    Jun. 24, 2021

Related U.S. Application Data

(60) Provisional application No. 62/951,170, filed on Dec. 20, 2019.

(51) Int. Cl.
*A61B 17/29* (2006.01)
*A61B 17/00* (2006.01)

(52) U.S. Cl.
CPC .... *A61B 17/29* (2013.01); *A61B 2017/00845* (2013.01); *A61B 2017/2926* (2013.01);
(Continued)

(58) Field of Classification Search
CPC ............ A61B 17/29; A61B 2017/2926; A61B 2017/2932; A61B 2017/2947;
(Continued)

(56) References Cited

U.S. PATENT DOCUMENTS 5,849,022 A    12/1998 Sakashita et al.
8,998,948 B2 *  4/2015 Hyodo ................... A61B 17/29
606/147
(Continued)

FOREIGN PATENT DOCUMENTS

WO    2016141200 A1    9/2016

OTHER PUBLICATIONS

International Search Report and Written Opinion from PCT/US2020/065542 dated Mar. 18, 2021.
SpyGlass DS System ebrochure (12 pages).

*Primary Examiner* — Timothy J Neal
*Assistant Examiner* — Mitchell Brian Hoag
(74) *Attorney, Agent, or Firm* — Calfee, Halter & Griswold LLP

(57) ABSTRACT

An endoscopic grasping device for use during an endoscopic procedure. The device includes at least a fork operably connected to a pair of jaws pivotally mounted about a pivot point to the fork. A pusher is disposed within the fork and operably connected to a drive wire and a pair of arms. Each arm is attached to a respective jaw and configured to move that jaw upon a movement of the pusher in a distal direction or proximal direction resulting in the pair of jaws being in a closed position and a open position. Each jaw includes a plurality of teeth extending therefrom and towards the opposite jaw. One or more of the teeth are backwards curved and angled in a proximal direction from the jaw to improve a grasping, cutting, and handling feature of the teeth.

9 Claims, 20 Drawing Sheets

(52) U.S. Cl.
CPC ............. *A61B 2017/2932* (2013.01); *A61B 2017/2933* (2013.01); *A61B 2017/2936* (2013.01); *A61B 2017/2939* (2013.01); *A61B 2017/2947* (2013.01)

(58) Field of Classification Search
CPC .... A61B 2017/2936; A61B 2017/2939; A61B 2017/00845; A61B 2017/2933; A61B 17/22031
USPC ........................................................ 606/207
See application file for complete search history.

(56) References Cited

U.S. PATENT DOCUMENTS

| | | |
|---|---|---|
| 2008/0294178 A1 | 11/2008 | Kortenbach et al. |
| 2014/0330308 A1* | 11/2014 | Hart ..................... A61B 17/29 606/207 |
| 2015/0066076 A1* | 3/2015 | Kerr .................... A61B 17/282 606/207 |
| 2015/0313581 A1* | 11/2015 | Wolfe .................... A61B 10/06 600/567 |
| 2015/0313621 A1* | 11/2015 | John .................. A61B 17/0467 606/206 |
| 2016/0100851 A1 | 4/2016 | Van Andel |
| 2016/0256140 A1 | 9/2016 | Haack et al. |
| 2016/0278801 A1* | 9/2016 | Michelini .............. A61B 17/29 |
| 2016/0296274 A1* | 10/2016 | Mensch ............. A61B 18/1442 |
| 2019/0150968 A1* | 5/2019 | Winstanley ........... A61B 10/06 |
| 2019/0183484 A1* | 6/2019 | Malkowski ........ A61B 17/0625 |
| 2021/0315600 A1* | 10/2021 | Peter ................ A61B 17/22031 |

\* cited by examiner

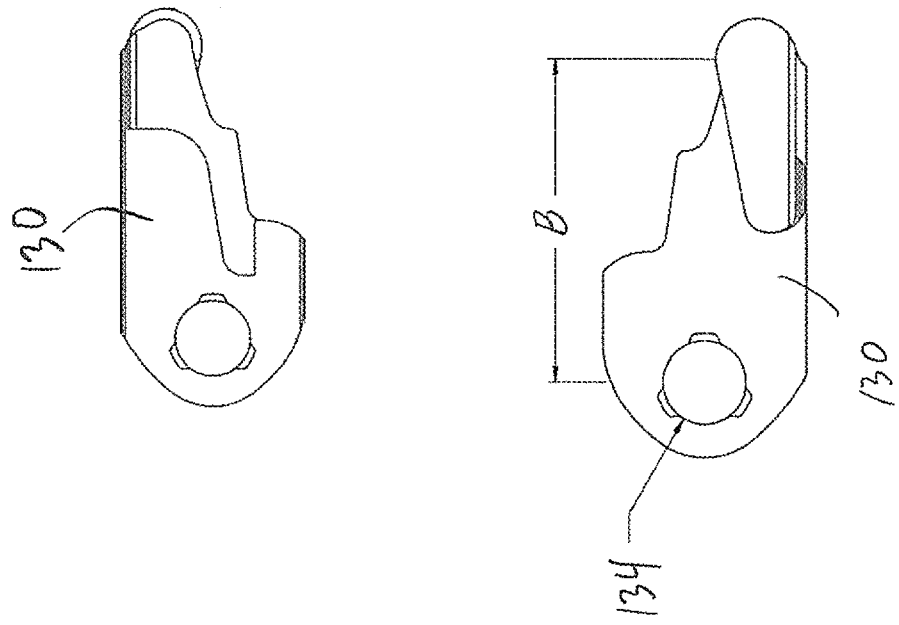
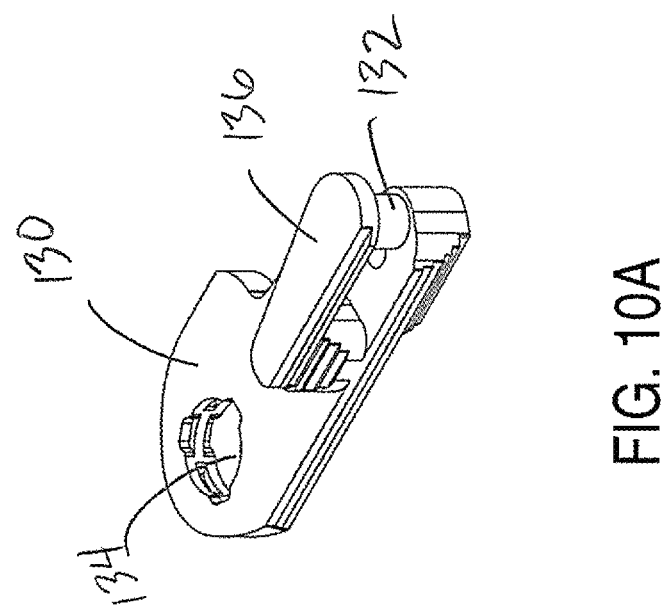
FIG. 10A
FIG. 10B

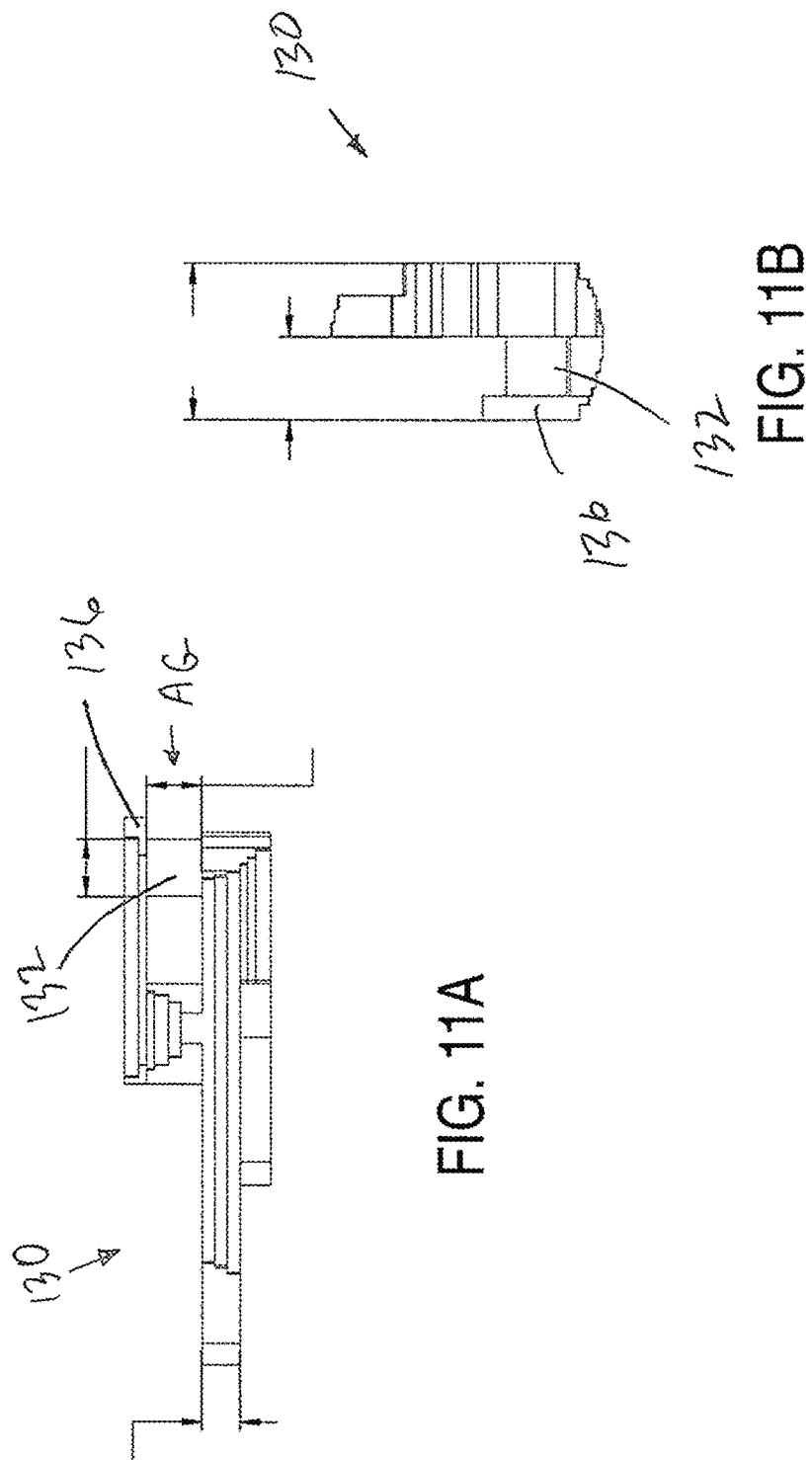

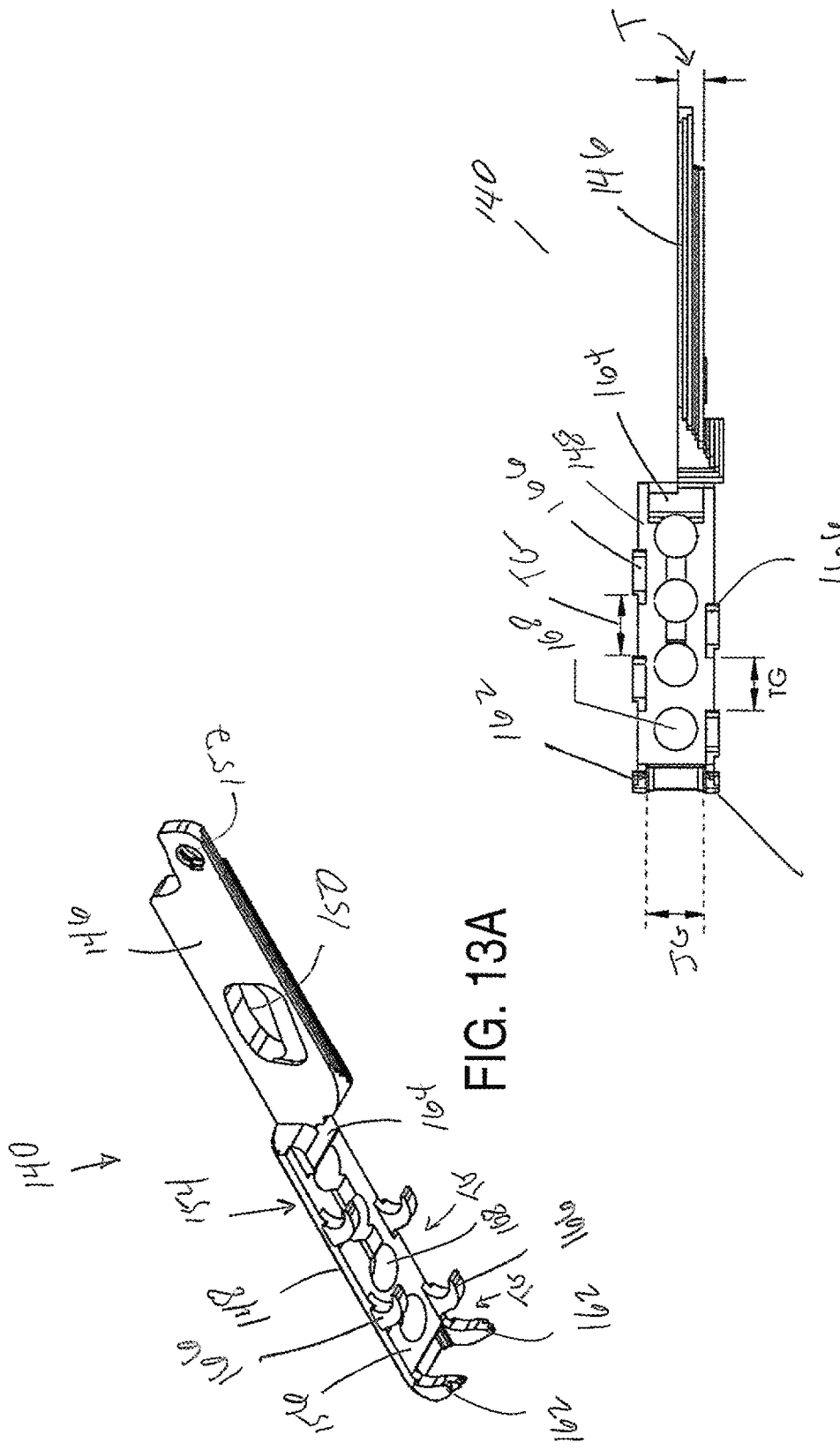

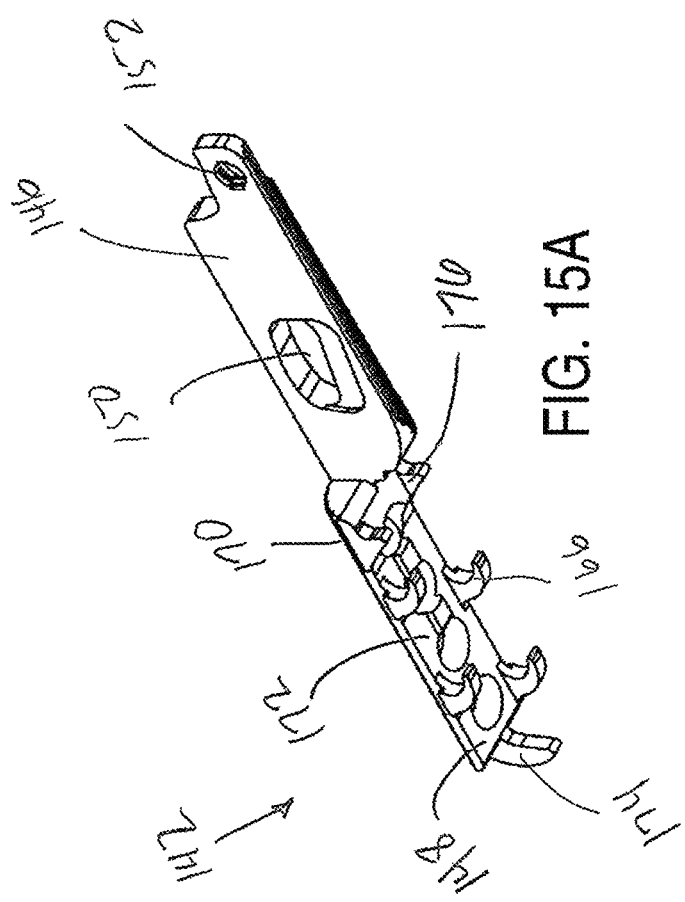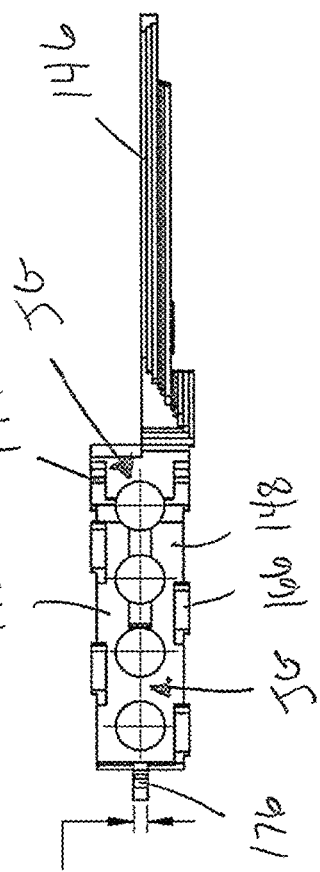
FIG. 15A
FIG. 15B

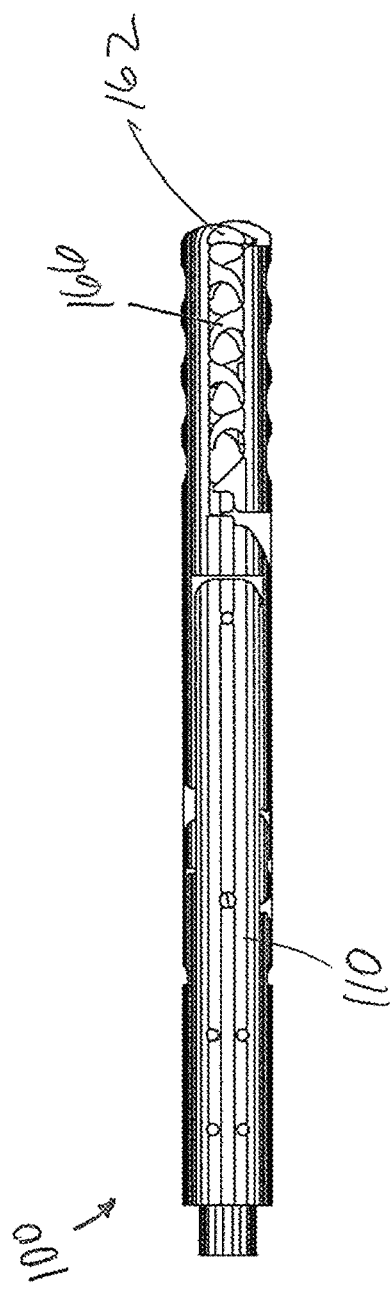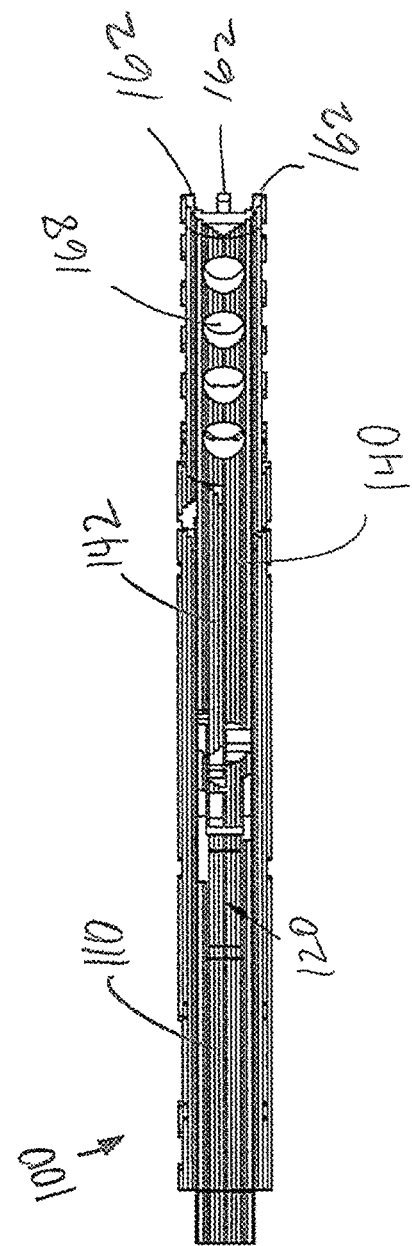
FIG. 16A
FIG. 16B

MICROFORCEPS

CROSS-REFERENCE TO RELATED APPLICATIONS

The present application claims benefits and priority to U.S. Provisional Patent Application No. 62/951,170, filed on Dec. 20, 2019, the entire disclosure of which is incorporated herein by reference.

TECHNICAL FIELD

The present disclosure generally relates to the field of biopsy and, more specifically, to forceps deployable through a needle.

BACKGROUND

Endoscopes are well-known in the medical arts and are commonly used for numerous medical procedures. One such procedure is removing objects from the inside of a human subject, such as for example, foreign bodies, excised human tissues from the wall of the gastrointestinal tract, and previously inserted medical objects, such as stents. One conventional technique for removing objects is using a grasping tool in an endoscopic procedure. Conventional endoscopic grasping devices have one or two jaws which pivot relative to a base. The jaw or jaws at the distal end of the device may be pivoted by a user operating a handle at a proximal end of the device and at a proximal location outside of the endoscope. The object may be held by the jaws while the endoscope, grasping device, and object are removed from the patient. The success of the user to grasp and retain objects during the procedure is dependent on several factors, including the shape and structure of the jaws (and the jaw teeth).

SUMMARY

In one exemplary embodiment, an endoscopy device is provided. The endoscopy device includes at least a fork defining a guide channel, a pair of control arms pivotally mounted about the fork at a proximal end of the guide channel, and a pair of jaws movable between a closed position and open position. Each jaw includes a grasping portion having a plurality of teeth and a connection portion. The grasping portion includes at least a front tooth formed at a distal end of the grasping portion, and a plurality of rear teeth formed between the front tooth and a proximal end of the grasping portion. The connection portion includes a first opening at a distal end of the connection portion and a second opening at a proximal end of the connection portion. The first opening is elongated and each jaw is pivotally mount at a distal end of the guide channel via the first opening, and each jaw is pivotally mounted to one of the pair of control arms via the second opening.

In another exemplary embodiment, a microforceps assembly is provided. The microforceps assembly includes at least a fork and two jaws pivotally mounted about a pivot point at a distal end of the fork and movable between an open position and a closed position. Each jaw includes a connection portion and a grasping portion. The connection portion of each jaw is mounted at the pivot point at the distal end. The grasping portion includes at least a front tooth, an intermediate tooth, and a rear tooth. One or more of the intermediate tooth and the rear tooth are curved in a proximal direction towards the connection portion.

In yet a further exemplary embodiment, a microforceps jaw is provided. The microforceps jaw includes at least a jaw body having a grasping portion and a connection portion. The grasping portion is wider than the connection portion and includes a plurality of teeth extending from the jaw body. The connection portion includes a pair of differently shaped recessed areas or openings for connecting the jaw to parts of an endoscopy device. At least one of the differently shaped recessed area or opening is elongated.

These and other objects, features and advantages of the present disclosure will become apparent from the following detailed description of illustrative embodiments thereof, which is to be read in connection with the accompanying drawings.

BRIEF DESCRIPTION OF THE DRAWINGS

These and other features of the present disclosure will become better understood with regard to the following description and accompanying drawings in which:

FIG. 10A illustrates a perspective view of an exemplary embodiment of an arm in accordance with the disclosure provided herein;

FIG. 10B illustrates side views of an exemplary embodiment of the arm of FIG. 10A;

FIG. 11A illustrates a top view of an exemplary embodiment of the arm of FIG. 10A;

FIG. 11B illustrates a front view of an exemplary embodiment of the arm of FIG. 10A;

FIG. 13A illustrates a perspective view of an exemplary embodiment of a jaw in accordance with the disclosure provided herein;

FIG. 13B illustrates an underside view of an exemplary embodiment of the jaw of FIG. 13A;

FIG. 15A illustrates a perspective view of another exemplary embodiment of a jaw in accordance with the disclosure provided herein;

FIG. 15B illustrates an underside view of an exemplary embodiment of the jaw of FIG. 15A;

FIG. 16A illustrates a side view of an embodiment of a microforceps assembly in a closed position, and in accordance with the disclosure provided herein;

FIG. 16B illustrates a top view of an embodiment of a microforceps assembly in an open position, and in accordance with the disclosure provided herein;

DETAILED DESCRIPTION

Aspects and implementations of the present disclosure will be understood more fully from the detailed description given below and from the accompanying drawings of the various aspects and implementations of the disclosure. This should not be taken to limit the disclosure to the specific aspects or implementations, but explanation and understanding only.

In discussing the exemplary embodiments herein, the terms "proximal" and "distal" are often used. These terms are used to describe a position or a direction with reference to the operator of the device. For example, the proximal position or proximal direction is toward the user or operator of the tool, and the distal position or direction is away from the user or operator of the tool, i.e., position or direction toward the object which the operator is attempting to grasp and retain.

Figure 1:
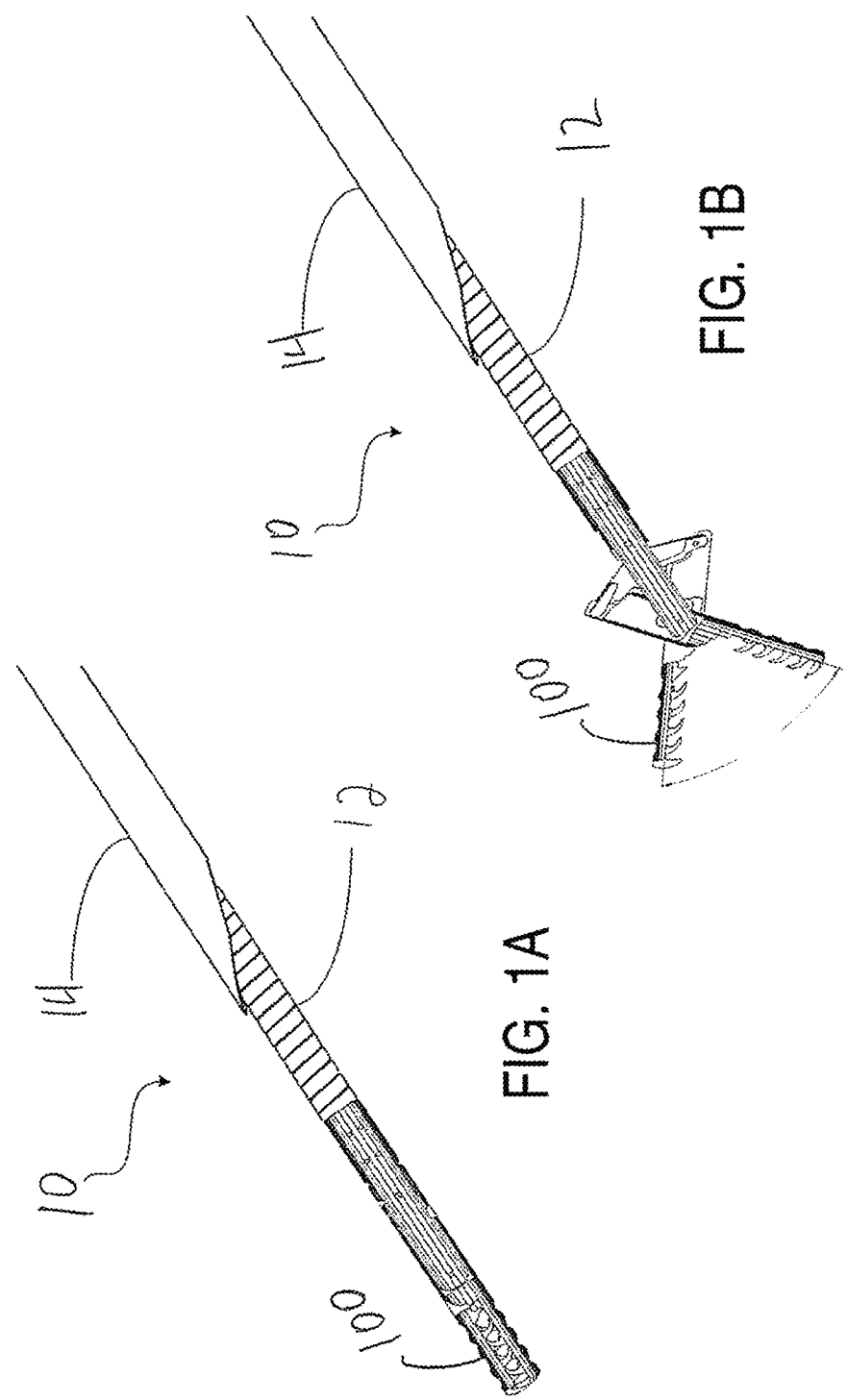
FIG. 1A illustrates an exemplary embodiment of an endoscopic grasping device in a closed position, and in accordance with the disclosure provided herein.
FIG. 1B illustrates an exemplary embodiment of the endoscopic grasping device of FIG. 1A in an open position.

Referring now to the drawings, which are for purposes of illustrating exemplary embodiments of the subject matter herein only, and not for limiting the same, FIG. 1A and FIG. 1B show an exemplary embodiment of an endoscopic grasping device 10 which may be used during an endoscopy ultrasound (EUS) procedure.

As shown in the figures, the endoscopic grasping device 10 may include at least a forceps assembly (e.g., a microforceps assembly 100), a sheath 12, and a needle 14. In the embodiment of FIG. 1A and FIG. 1B, the endoscopic grasping device 10 is shown with at least one embodiment of the microforceps assembly 100 in a closed position (FIG. 1A) and an open position (FIG. 1B).

In some embodiments, the jaws of the microforceps assembly 100 may open between 0°-120°. In a further embodiment, a diameter of the microforceps assembly 100 may be between 0.013 to 0.160 inches when the jaws of the microforceps assembly 100 are in the closed position. Additionally, or alternatively, the diameter of the microforceps assembly 100 may be between 0.013 to 0.023 inches, for example, when used with a 22 gauge needle.

With continued reference to FIG. 1A and FIG. 1B, the microforceps assembly 100 is shown extending in a distal direction from the sheath 12 of the needle 14. In some embodiments, the endoscopic grasping device 10 may further include one or more control wires or drive wires (not shown). The drive wires may be operably connected to one or more jaws of the microforceps assembly 100, for example, through the sheath 12 and towards the proximal end of the endoscopic grasping device 10, for facilitating the opening and closing of the jaws. For example, a movement of the drive wire(s) in the distal direction may open the jaws as shown in FIG. 1B, while a movement of the drive wire(s) in the proximal direction may close the jaws as shown in FIG. 1A. The drive wire may be formed from stainless steel materials and/or other materials suitable for performing the functions of the drive wire and connectable to parts of the microforceps assembly 100 (e.g., a nickel titanium such as Nitinol). In some embodiments, the suitable materials may include any medical grade materials (i.e., materials safe for use in a medical application).

In some embodiments, the sheath 12 may be a spring sheath catheter, a solid tube, or a tube with laser cuts. The sheath 12 may run the length of the endoscopic grasping device 10, for example, from the microforceps assembly 100 (or portions thereof (e.g., a fork)) to a handle assembly 20 of the endoscopic grasping device 10. The sheath 12 may be formed of a coil wire and may be a variety of shapes, such as for example, a circular cross section or a rectangular cross section. In some embodiments, the sheath 12 may be PTFE (Teflon) coated or a heat shrink coated (e.g., on its outside). The diameter of the sheath 12 may vary and be based on a diameter of the needle 14. In some embodiments, an outside diameter range of the sheath 12 may be between 0.013 to 0.160 inches. Additionally, or alternatively, the diameter may be between 0.013 to 0.023 inches, for example, when used with a 22 gauge needle.

It should be appreciated that the sheath 12 may be long enough to allow for a reasonable length beyond the proximal end and/or beyond the distal end of an endoscope. It should be further appreciated that the length of the sheath 12 may be based on a total working length of the endoscopic grasping device 10. In some embodiments, for example, a length of the sheath 12 may be between 43 to 138 inches. In some embodiments, the drive wire within the sheath 12 may run the length of the endoscopic grasping device 10.

The inside of the sheath 12 may include or be formed from a lubricious material, such as a High-density polyethylene (HDPE) or other thermoplastic polymers, or in some embodiments, the sheath 12 may include a tubing of some lubricious material, such as HDPE, running through the length of the endoscopic grasping device 10. It should be appreciated that the tubing may reduce metal-on-metal contact between the sheath 12 and the drive wire, which may further reduce wear and provide for a smoother operation of the endoscopic grasping device 10. It should further be appreciated that other friction-reducing structure(s) may be used.

In some embodiments, the needle 14 may be a 22 gauge hollow needle. It should be appreciated that embodiments of the microforceps assembly 100 disclosed herein may be sized or otherwise shaped for being disposed (e.g., at least partially disposed) within the 22 gauge needle. It should further be appreciated that due to the size of the needle 14, one or more parts of the microforceps assembly 100 (or the device itself) may be fabricated via a micromachining process, metal injection molding process, a ceramic injection molding process, a stamping process, or other process configurable to fabricate microforceps of a same or similar size for use with, e.g., the 22 gauge needle.

Figure 2:
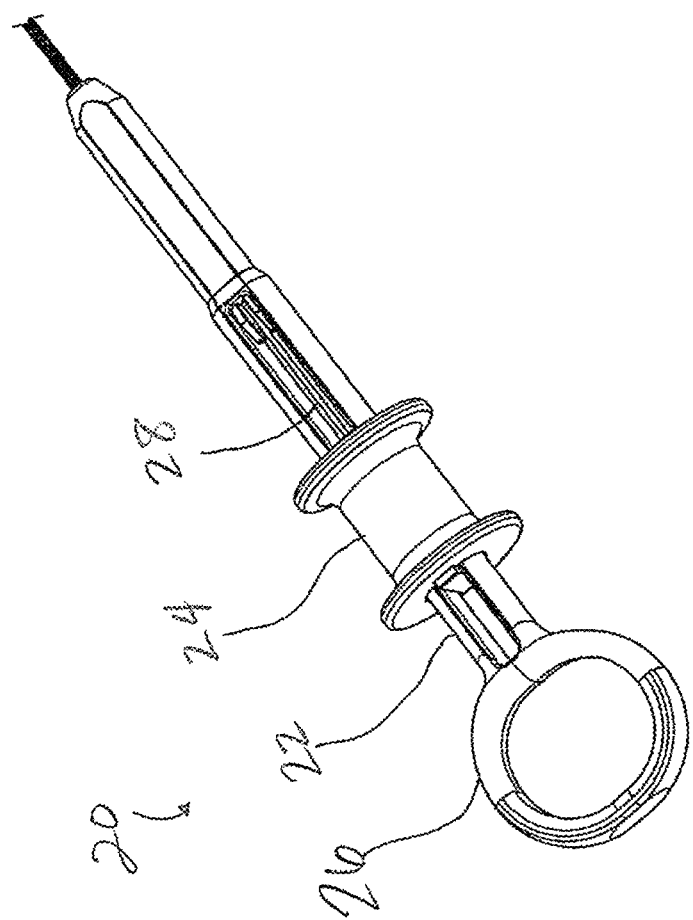
FIG. 2 illustrates an exemplary embodiment of a handle assembly in accordance with the disclosure provided herein.

With reference now to FIG. 2, the endoscopic grasping device 10 may be operably connected to a handle assembly 20 for operably controlling the grasping function (e.g., an opening and closing) of the microforceps assembly 100 in operation. The handle assembly 20 may be at the proximal end of the endoscopic grasping device 10. In some embodiments, the handle assembly 20 may include at least a base 22 and a slider 24. The handle assembly 20 may be used to transfer a linear motion of the slider 24 to open and close jaws of the microforceps assembly 100 at the distal end of the endoscopic grasping device 10. In some embodiments, the handle assembly 20 may include a ring 26 and link 28 for operably opening and closing the jaws.

In operation, a user may insert a thumb from one hand into the ring 26 and rest several fingers (e.g., from the same hand) on, or around the slider 24. The link 28 may be attached directly or indirectly to the drive wire within the sheath 12. Moving the slider 24 relative to the base 22 may cause the link 28 to move. Consequently, the user may open the jaws by actuating the slider 24 and moving it, for example, in the distal direction, and may close the jaws by moving the slider, for example, in the proximal direction. It should be apparent to one skilled in the art that the design and operation of the handle assembly 20 and the link 28 to the control and/or drive wire may vary in the practice of this invention.

Figure 3:
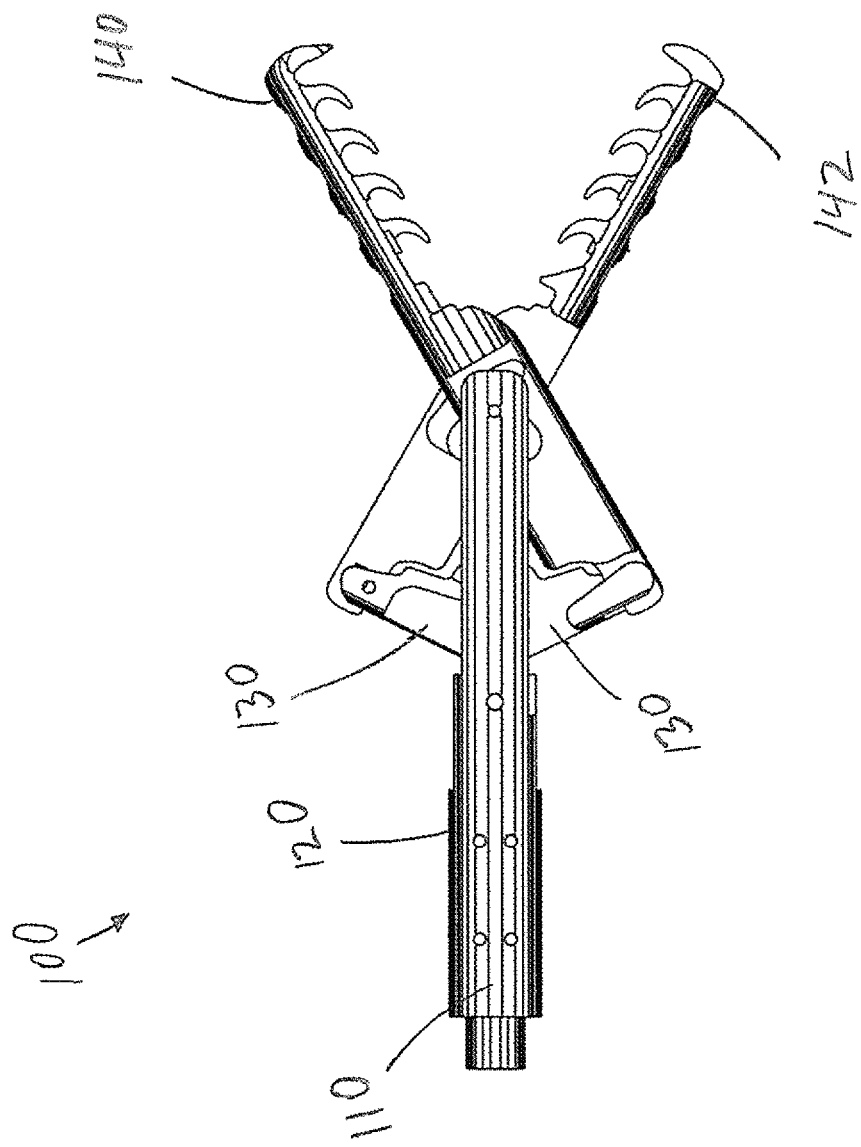
FIG. 3 illustrates an exemplary embodiment of a microforceps assembly in accordance with the disclosure provided herein.
Figure 4:
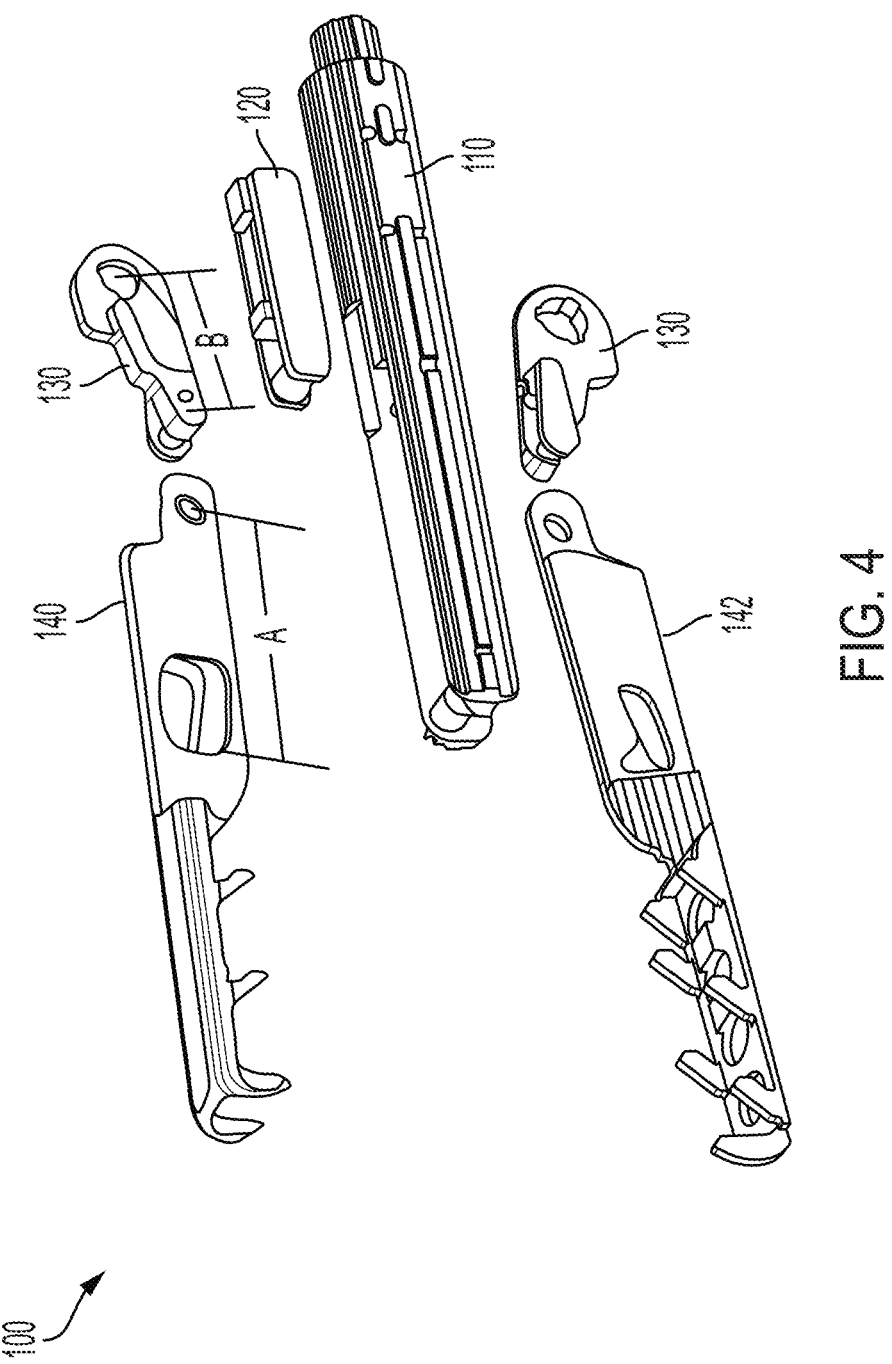
FIG. 4 illustrates an exploded view of an exemplary embodiment of a microforceps assembly in accordance with the disclosure provided herein.

With reference now to FIG. 3 and FIG. 4, the microforceps assembly 100 may include at least a fork 110, and in some embodiments, a pusher 120 operably connected to one or more arms 130 (two shown in FIG. 3) and a first jaw 140 and second jaw 142.

As illustrated in FIG. 4, and to improve the closing force of the jaws in operation, length A of the first jaw 140 and/or second jaw 142 may be greater than length B of one or more of the arms 130.

Figure 12A:
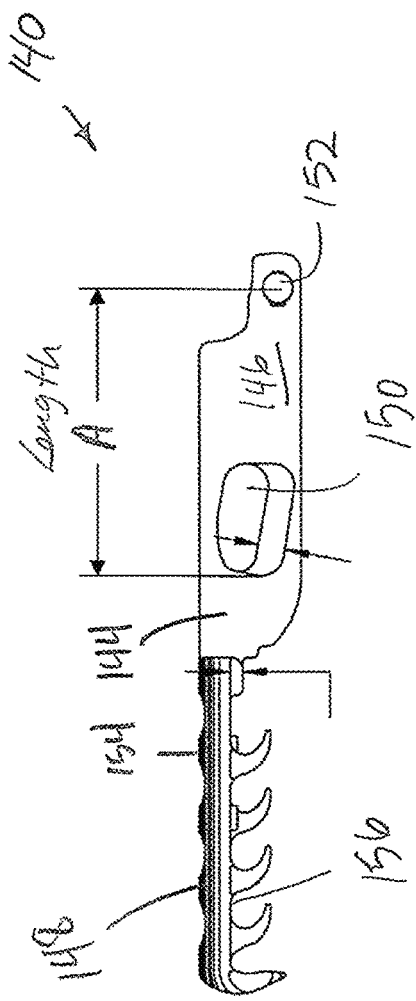
FIG. 12A illustrates a perspective view of an exemplary embodiment of a jaw in accordance with the disclosure provided herein.
Figure 12B:
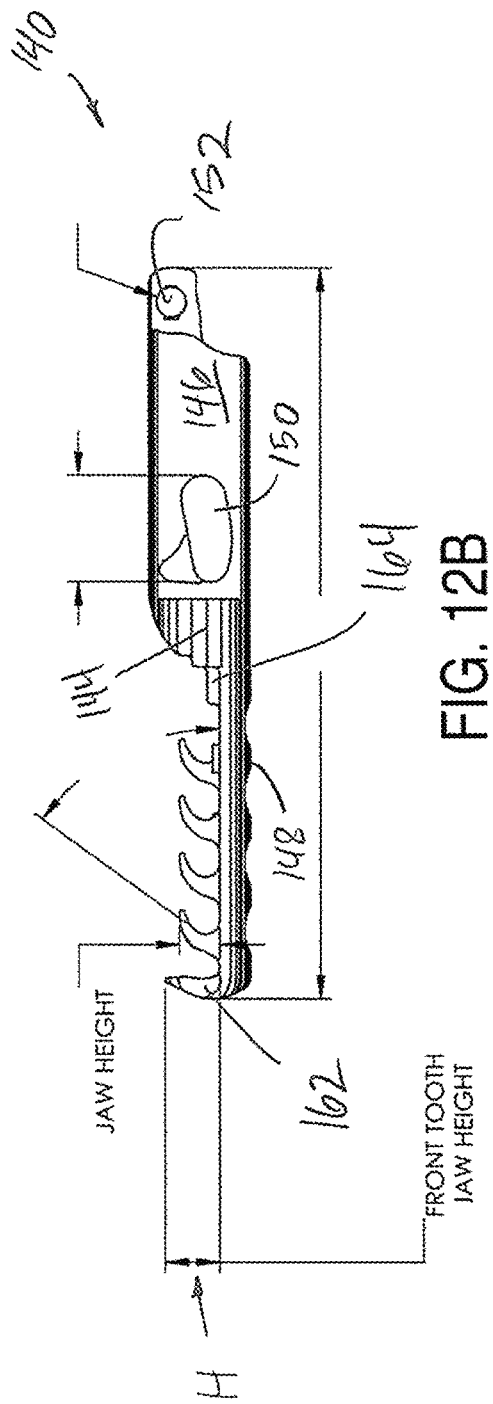
FIG. 12B illustrates a second perspective view of the jaw of FIG. 12A.

In some embodiments, length A may be the distance between a first point of a first opening in the jaw and a second point of a second opening in the same jaw. For example, FIG. 4 (and also FIG. 12A) shows length A measured from a distal point of a first opening 150 to a point of a second opening 152, which may be at or near a center of the second opening 152. Additionally, or alternatively, length A may be measured between a center point of the first opening 150 and a point of the second opening 152.

In some embodiments, length B may be the distance between a first point at one end of the arm 130 (e.g., where the arm 130 may be pivotally connected to the jaw) and a second point at an opposite end of the arm 130. In the embodiment of FIG. 4 (and also FIG. 10B), length B is shown measured between a center point of an arm pin 132 at a distal end of the arm 130 and a center point of an opening (e.g., a first opening 134) at a proximal end of the arm 130, for example, where the arm 130 may be connectable to the fork 110 and/or a pusher 120.

It should be appreciated that length A and/or length B may be measured from one or more points or areas proximate to and/or surrounding a center point of the openings described above.

With reference now to FIG. 5 and FIG. 6A-FIG. 6D, the fork 110 may include one or more guide channels 112. In some embodiments, portions of the guide channel 112 (e.g., at a proximal end of the guide channel 112) may be sized or otherwise shaped for receiving at least a portion of the pusher 120 therebetween. Additionally, or alternatively, portions of the guide channel 112 may be sized or otherwise shaped for receiving portions of one or more of the remaining parts of the microforceps assembly 100 therebetween (e.g., one or more arms 130 and/or first jaw 140 and second jaw 142).

Figure 5:
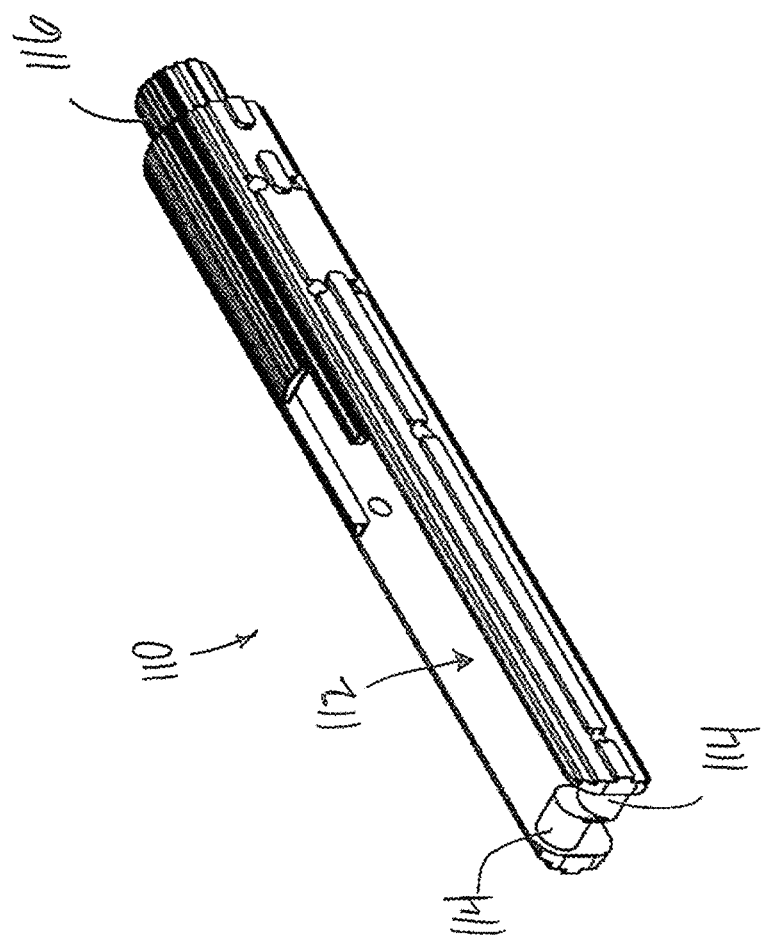
FIG. 5 illustrates an exemplary embodiment of a fork in accordance with the disclosure provided herein.
Figure 6A:
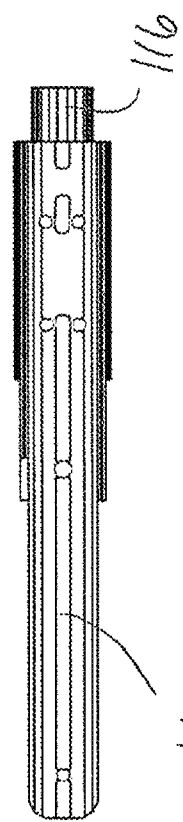
FIG. 6A illustrates a side view of an exemplary embodiment of a fork in accordance with the disclosure provided herein.
Figure 6B:
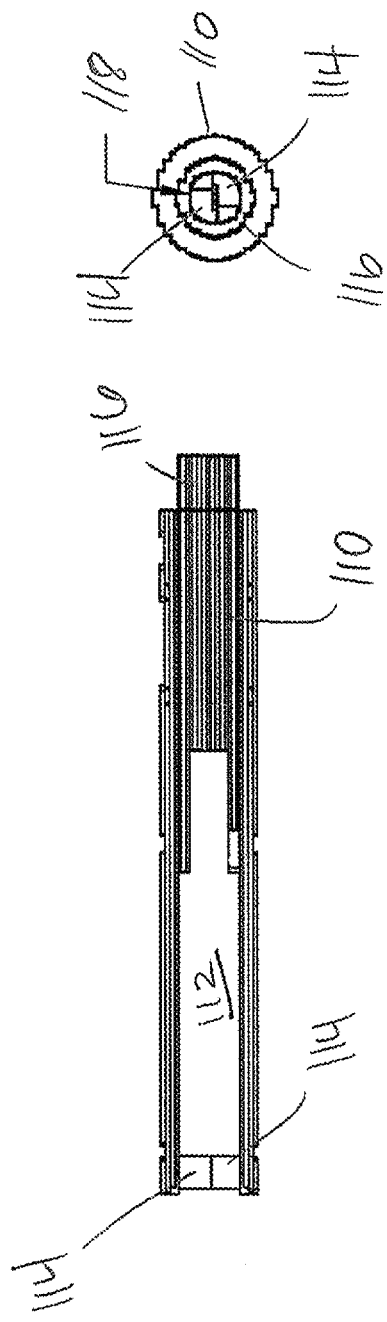
FIG. 6B illustrates a top view of an exemplary embodiment of a fork in accordance with the disclosure provided herein.
Figure 6C:
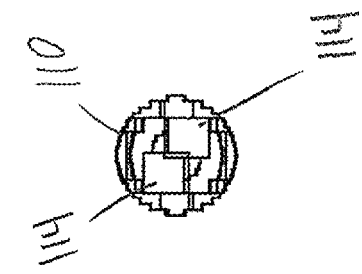
FIG. 6C illustrates a perspective view of a distal end of an exemplary embodiment of a fork in accordance with the disclosure provided herein.
Figure 6D:
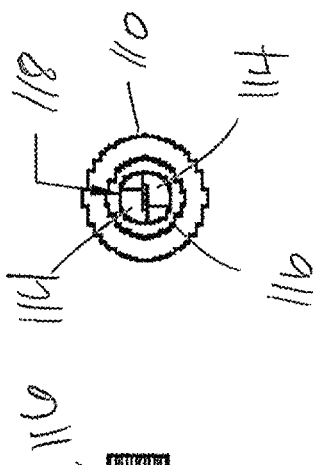
FIG. 6D illustrates a perspective view of a proximal end of an exemplary embodiment of a fork in accordance with the disclosure provided herein.
Figure 7B:
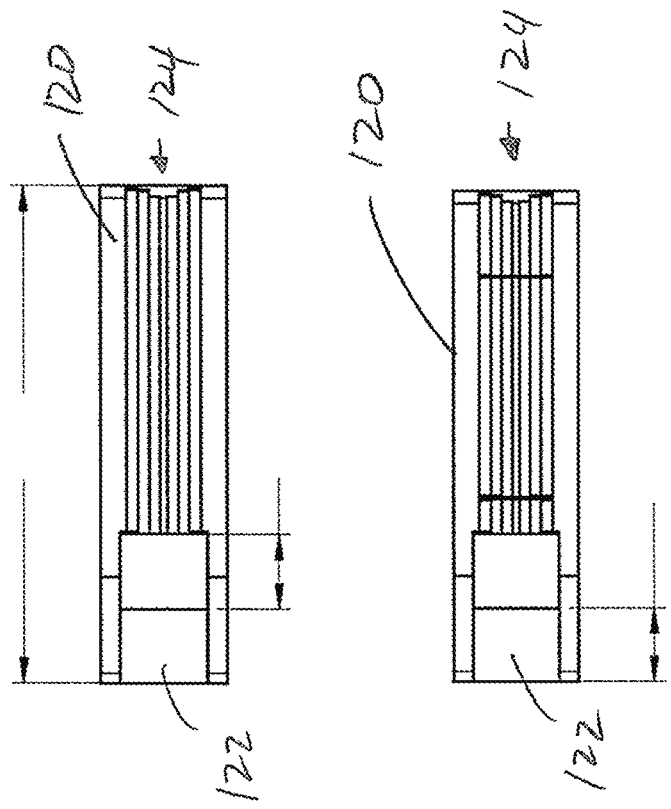
FIG. 7B illustrates a top view and bottom view of an exemplary embodiment of a pusher in accordance with the disclosure provided herein.
Figure 7A:
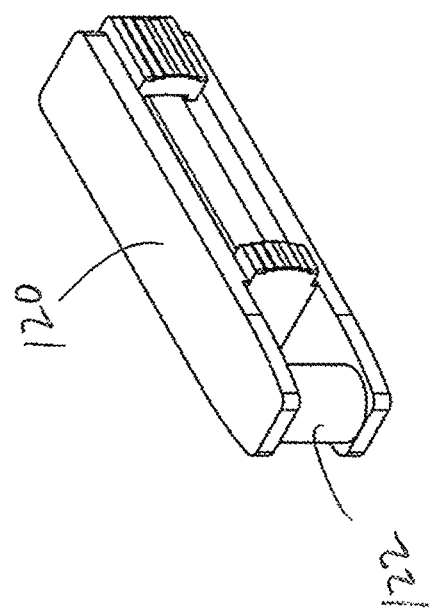
FIG. 7A illustrates a perspective view of an exemplary embodiment of a pusher in accordance with the disclosure provided herein.
Figure 8C:
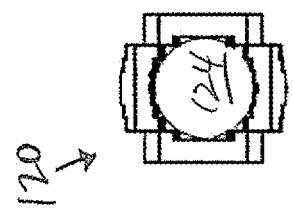
FIG. 8C illustrates a perspective view of a proximal end of an exemplary embodiment of a pusher in accordance with the disclosure provided herein.
Figure 8A:
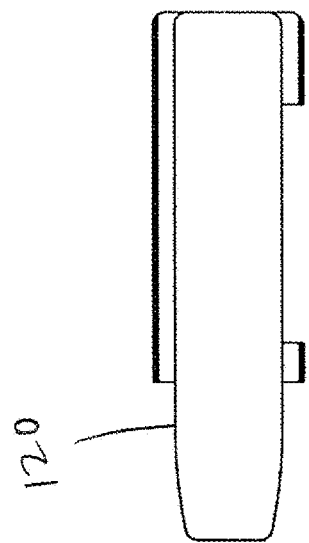
FIG. 8A illustrates a side view of an exemplary embodiment of a pusher in accordance with the disclosure provided herein.
Figure 8B:
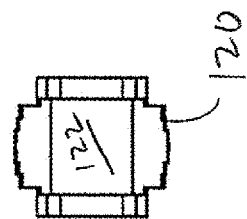
FIG. 8B illustrates a perspective view of a distal end of an exemplary embodiment of a pusher in accordance with the disclosure provided herein.

The fork 110 may include one or more fork pins 114 for connecting parts of the microforceps assembly 100. In the embodiment of FIG. 5, a pair of fork pins 114 may be provided at a distal end of the fork 110. In some embodiments, for example, as shown in FIG. 6C, the pair of fork pins 114 may be offset from one another. It should be appreciated that offset fork pins 114 provides a mechanical advantage and improves the closing force of the microforceps assembly 100 in operation. For example, the offset fork pins 114 may raise the point of leverage during operation, so when the pusher 120 pulls in the proximal directions, the arm 130 pushes down resulting in an increased closing force.

Additionally, or alternatively, each fork pin 114 may be sized or otherwise shaped for being at least partially received between openings within the jaws and/or arms of the microforceps assembly 100 so that the jaws and/or arms may pivot therefrom when operably connected to the fork 110. In some embodiments, the fork pin 114 may be secure to or formed on an inside wall of the fork 110 within the guide channel 112.

With continue reference to the figures, the fork 110 may include a collar 116 at the proximal end of the fork 110. The distal end of the sheath 12 may be attached to the fork 110 at the collar 116. The collar 116 may include an opening 118 for receiving the drive wire therebetween and into the guide channel 112 for connecting the drive wire (e.g., via weld) to portions of the pusher 120. The opening 118 may extend from the proximal end of the fork 110 through the collar 116 and into the guide channel 112 to allow for the drive wire to connect to the pusher 120 via the collar 116.

Figure 20:
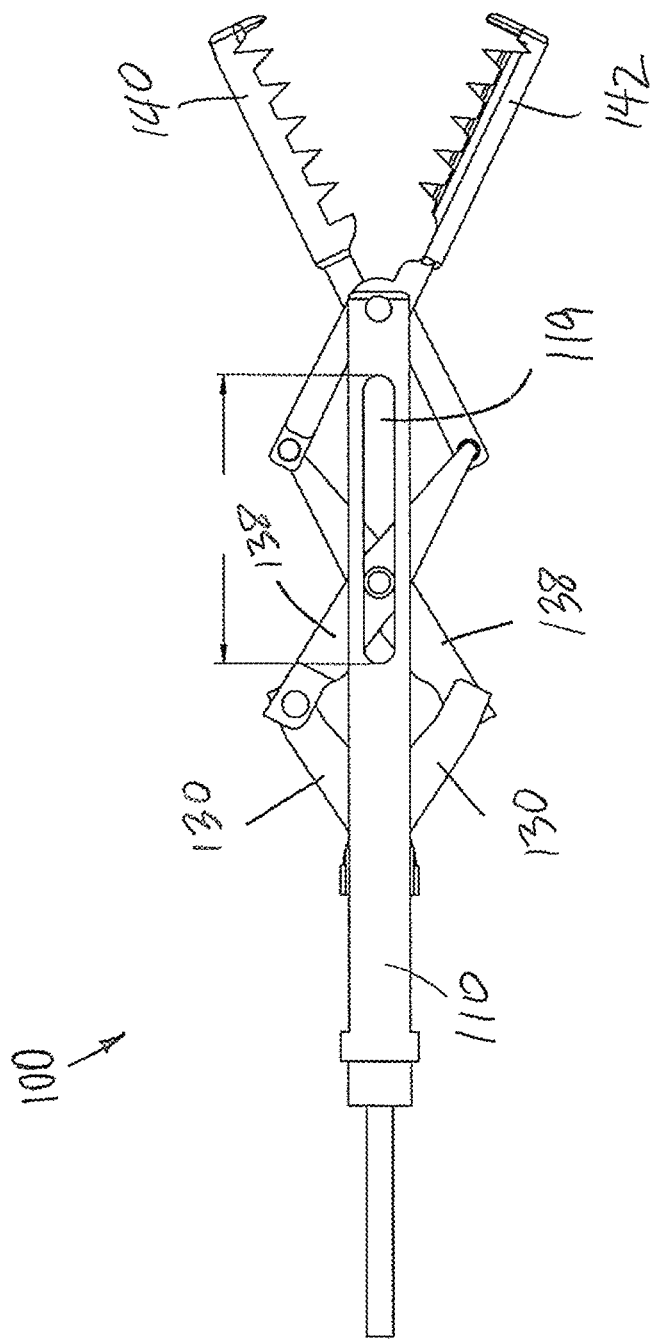
FIG. 20 illustrates a side view of yet a further exemplary embodiment of a microforceps assembly in accordance with the disclosure provided herein.

Additionally, or alternatively, the fork 110 may include one or more openings or slots 119 (FIG. 20) in opposed sides of the fork 110. Each slot 119 may be sized or otherwise shaped to allow for a movement (e.g., a slidable movement) of one or more arms 130 (or arm extensions 138) operably connected to the fork 110 via the slot 119 when opening and closing the jaws of the microforceps assembly 100 in operation. In some embodiments, the slot 119 may be elongated.

It should be appreciated that the slot 119 (e.g., the elongated slot) provides a mechanical advantage by allowing for an improved opening width of the jaws based on the slidable movement within the slot 119, and also improves/increases the closing force of the jaws. It should further be appreciated that the slot 119 may assist with aligning one or more parts of the microforceps assembly 100 (e.g., the arm 130 and/or pusher 120) in operation.

In some embodiments, the slot 119 allows for a shorter arm 130 to be provided without sacrificing the opening width of the jaws. A shorter arm 130 may increase the downward force on the arm pin 132, which increases the closing force on the jaws.

With reference now to FIG. 7A-FIG. 7B and FIG. 8A-FIG. 8C, the pusher 120 may be sized or otherwise shaped to be at least partially disposed within the guide channel 112. It should be appreciated that the portions of the fork 110 (e.g., the guide channel 112) may be arranged (or designed) to keep the pusher 120 in a substantially straight line for the entire stroke of the endoscopic grasping device 10 in operation.

In some embodiments, the pusher 120 may include one or more pusher pins 122 at a distal end of the pusher 120. The pusher pin 122 may be sized or otherwise shaped to be at least partially disposed between an opening in the arm 130 for pivotably connecting the arm 130 thereto.

Additionally, or alternatively, the pusher 120 may include one or more openings or recessed areas. In one embodiment, an opening 124 may be formed at a proximal end of the pusher for receiving, for example, the drive wire therethrough. The drive wire may be disposed between the opening 124 at a proximal end of the pusher 120 and may be welded or otherwise affixed to the pusher 120.

Additionally, or alternatively, a gap may be formed in the pusher 120. The pusher 120 may be placed or otherwise positioned within the guide channel 112 such that the pusher 120 may then move (e.g., slide) within the guide channel 112 from a proximal end of the guide channel to a distal end of the guide channel 112.

In operation, for example, a movement of the pusher 120 within the guide channel 112 in a distal direction may result in the jaws being opened, while a movement of the pusher 120 in a proximal direction may result in the jaws being closed. Additionally, the jaws may be opened via two separate pins that push outward to open the jaws and pulled inward to close the jaws.

Figure 9B:
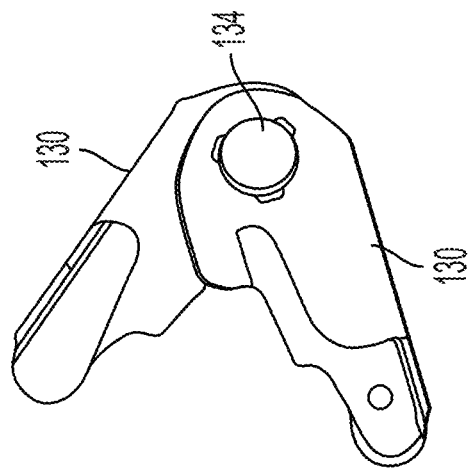
FIG. 9B illustrates a side view of an exemplary embodiment of the pair of arms of FIG. 9A.
Figure 9A:
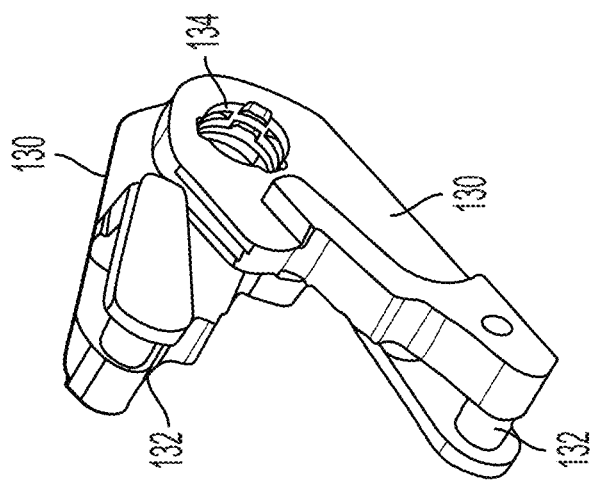
FIG. 9A illustrates a perspective view of an exemplary embodiment of a pair of arms of a microforceps assembly in accordance with the disclosure provided herein.

With continued reference to the figures, and now with reference to FIG. 9-FIG. 11, the arm 130 may include an arm pin 132 disposed at or near a distal end of the arm 130. Additionally, or alternatively, the arm 130 may include one or more openings, including at least a first opening 134 at a proximal end of the arm 130.

The arm pin 132 may be sized or otherwise shaped for connecting (e.g., pivotably connecting) the arm 130 to at least one of the first jaw 140 and/or second jaw 142. The first opening 134 may be sized or otherwise shaped for receiving at least a portion of the pusher 120 (e.g., the pusher pin 122) therebetween.

In some embodiments, the arm 130 may include a shoulder 136. The shoulder 136 may protrude or otherwise be formed from a side of the arm 130 and may be arranged such that the arm pin may be disposed between the shoulder and a side of the arm 130 at the distal end. As shown in FIG. 10A, the shoulder 136 may protrude at or near a center of the arm 130 and may extend in a distal direction towards the distal end of the arm 130. In some embodiments, a distal end of the shoulder 136 may extend beyond the distal end of the arm 130.

With continued reference to the figures, and now with reference to FIG. 12-FIG. 15, exemplary embodiments of the first jaw 140 and second jaw 142 are illustrated. As illustrated in the figures, each jaw includes at least a jaw body 144 having a connection portion 146 and a grasping portion 148. In some embodiments, the connection portion 146 may have a thickness T (FIG. 13B) less than a width of the grasping portion 148. In some embodiment, the combined thickness of the connection portions 146 for the first jaw 140 and second jaw 142 may be equal to or less than a width of any one jaw grasping portion 148.

The connection portion 146 may include one or more openings at or near a distal end and/or proximal end of the connection portion 146. In some embodiments, a first opening 150 may be provided at or near a distal end of the connection portion 146. The first opening 150 may be sized for receiving at least a portion of the fork pin 114 therebetween and for connecting the fork 110 to the first jaw 140 and/or second jaw 142. The first opening 150 may be shaped to allow for a movement (pivoting and/or sliding movement) of the fork pin 114 within the first opening 150 in operation. In some embodiments, the first opening 150 may be elongated to provide for slidable movement.

Figure 19:
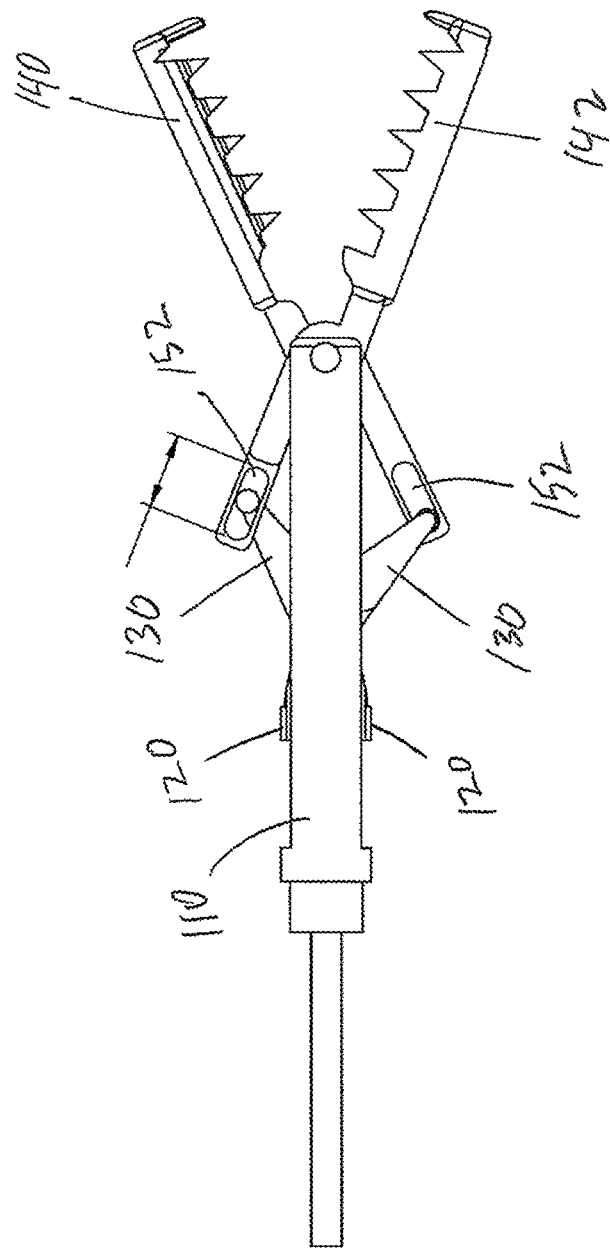
FIG. 19 illustrates a side view of yet another exemplary embodiment of a microforceps assembly in accordance with the disclosure provided herein.

With continued reference to the figures, a second opening 152 may be provided at or near a proximal end of the connection portion 146. In some embodiments, the second opening 152 may be sized or otherwise shaped for receiving at least a portion of the arm pin 132 therebetween. In some embodiments, the second opening 152 may be elongated (e.g., as shown in FIG. 19) to allow for movement (pivoting and/or sliding) of the arm pin 132 within the second opening 152 in operation. It should be appreciated that the described geometries for the openings (e.g., the first opening 150 and/or the second opening 152) allow for a greater opening width of the jaws while improving the closing force by allowing for the arm 130 to be fabricated as short as possible. In yet a further exemplary embodiment, the arm pin 132 may be elongated.

In some embodiments, a thickness T of the connection portion 146 may be equal to or less than an arm pin gap (AG of FIG. 11A) between the shoulder 136 and the arm 130 body from where the shoulder 136 protrudes.

With continue reference to the figures, the grasping portion 148 may include at least a topside 154, an underside 156, a distal end, and a proximal end. The proximal end of the grasping portion 148 may begin at or near the distal end of the jaw body 144. As illustrated in the figures, the grasping portion 148 of each jaw may include a plurality of teeth formed thereon or otherwise extending from an underside 156 of each jaw. As described herein, one or more teeth at a distal end of the grasping portion 148 may be referred to as a forward tooth and/or teeth 162 while one or more teeth at a proximal end of the grasping portion 148 of each jaw may be referred to a rear tooth and/or teeth 164.

In some embodiments, the first jaw 140 may include a pair of forward teeth 162 formed at or near the distal end of the grasping portion 148, and on opposed sides of the underside 156. It should be appreciated that each opposed side where any teeth may be formed may be referred to as a row of teeth, even if only one tooth may be provided in a particular row.

As illustrate in FIG. 13A, the forward teeth 162 may be aligned with each other on opposed sides of the grasping portion 148 at the distal end. In some embodiments, a jaw gap JG (FIG. 13B) may be defined or otherwise formed between the forward teeth 162. The jaw gap JG may extend from the distal end of the grasping portion 148 towards the proximal end of the grasping portion 148 where a rear tooth 164 may be formed, or in some embodiments, towards the distal end of the connection portion 146. In some embodiments, the rear tooth 164 may have a width corresponding to a width of the jaw gap JG.

With continued reference to the figures, the first jaw may include one or more intermediate teeth 166. The intermediate teeth 166 may be disposed in a row along opposed sides of the underside 156 of the grasping portion 148.

In some embodiments, the intermediate teeth 166 may be backward curved teeth (i.e., teeth curved or otherwise angled in the proximal direction). At least one intermediate tooth 166 may be adjacent to a forward tooth 162 on one side of the grasping portion 148 such that a tooth gap TG (FIG. 13A) is defined or otherwise formed between the forward tooth 162 and the adjacent intermediate teeth 166. In some embodiments, the tooth gap TG between a forward tooth 162 and a next intermediate tooth 166 may be less than the tooth gap between intermediate teeth 166 in the same row of teeth along the underside 156.

Additionally, or alternatively, a tooth gap TG between a forward tooth 162 and intermediate tooth 166 in one row may be different (e.g., equal to or less and/or equal to or greater) than a tooth gap TG between a forward tooth 162 and intermediate tooth 166 in a second opposite row. In some embodiments, the tooth gap TG between intermediate teeth 166 may be the same for each row of teeth. Additionally, or alternatively, the tooth gap TG between the rear tooth 164 and any intermediate teeth 166 on either row may be the same or vary.

With continue reference to the figures, the grasping portion 148 of one or more jaws may include one or more openings 168 (or similar fenestrations) extending through a thickness of the grasping portion 148 (i.e., through the topside 154 and underside 156).

In some embodiments, a diameter of each fenestration may be between 0.003 and 0.150 inches. Additionally, or alternatively, the diameter may be between 0.003 and 0.012 inches when used, for example, with a 22 gauge needle. In the embodiment of FIG. 13B, at least 4 fenestrations 168 are shown extending through the thickness of the grasping portion 148. In some embodiments, where multiple fenestrations are provided, a diameter for each fenestration 168, or one or more of the fenestrations 168 may be at or about 0.008 inches.

In the embodiment of FIG. 13B, the first jaw 140 is shown with four (4) openings 168 between the distal end and proximal end of the grasping portion 148. It should be appreciated that the series of openings 168 on the jaws may assist with capturing samples from the grasp of the microforceps assembly 100 after the MFA is removed from the patient. It should be appreciated that the fenestrations (i.e., openings 168) are provided to assist with removing samples after the microforceps assembly 100 has been removed from the patient by allowing for any samples to be pushed out via the fenestrations.

In some embodiments, the openings 168 may be spaced an equidistance apart from one another. Additionally, or alternatively, the openings 168 in the first jaw 140 may be aligned (fully or partially) with openings 168 in the second jaw 142.

With continued reference to the figures, a height H of the forward teeth 162 (FIG. 12B) may extend vertically pass a centerline of both the first jaw 140 and second jaw 142 when the first jaw and second jaw are operably connected. Additionally, or alternatively, the height of the intermediate teeth 166 may be less than a height of the forward teeth 162, and in some embodiments, greater than a height of the rear tooth 164 and/or teeth.

In some embodiments, one or more of the forward teeth 162 may extend in a vertical direction such that a tip of the forward teeth 162 points toward the underside of the opposed jaw. Additionally, or alternatively, one or more tips for the intermediate teeth 166 may be pointed in the proximal direction (i.e., towards the proximal end of the microforceps assembly 100).

Figure 14A:
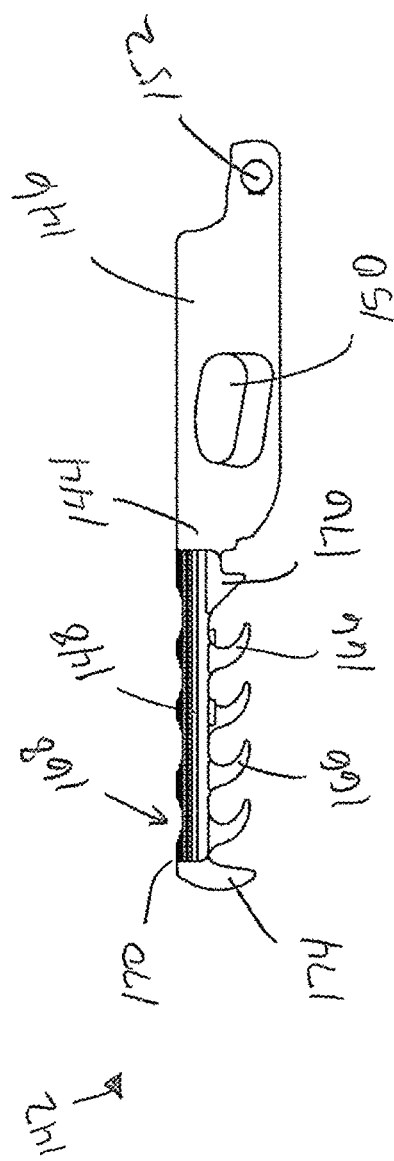
FIG. 14A illustrates a side view of another exemplary embodiment of a jaw in accordance with the disclosure provided herein.
Figure 14B:
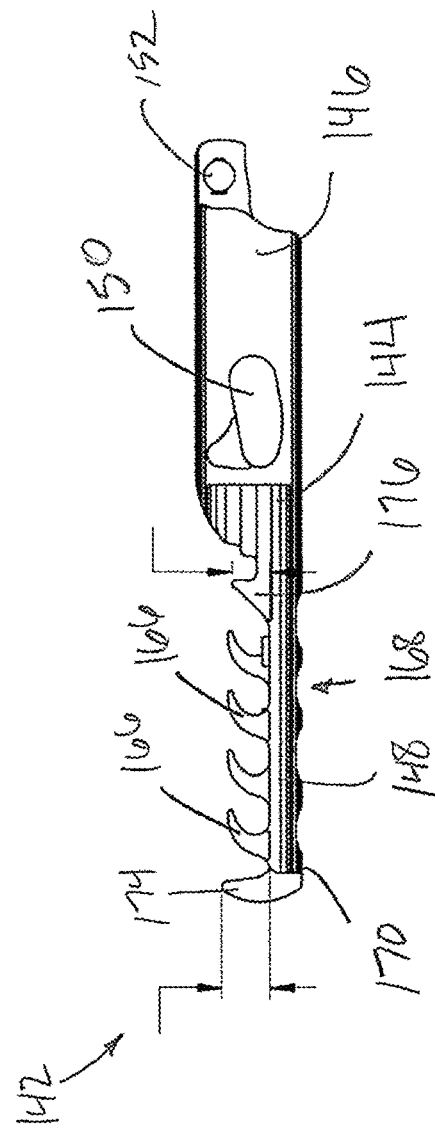
FIG. 14B illustrates a second side view of the jaw of FIG. 14A.

With reference to FIG. 14A and FIG. 14B, the second jaw 142 may include a topside 170 and underside 172. The underside 172 may include only one forward tooth 174 disposed at or near the distal end of the grasping portion 148. In some embodiments, the forward tooth 174 may be positioned at the distal end such that the forward tooth 174 may be seated between the forward teeth 162 when the first jaw 140 and second jaw 142 are operably connected (FIG. 16B) and in a closed position. In this embodiment, for example, the forward tooth 174 may be disposed at or near a center of the jaw gap JG (FIG. 15B) formed on the underside 172.

In some embodiments, the forward tooth 174 may extend from the underside 172 of the second jaw 142. Additionally, or alternatively, the forward tooth 174 may extend outwardly from the distal end of the second jaw 142 and not the underside 172. It should be appreciated that in an embodiment where the forward tooth 174 extends from the distal end of the second jaw 142, the distal most point of the forward tooth 174 may be aligned (fully or partially aligned) with the distal most point of the forward teeth 162 when the microforceps assembly 100 is in the closed position.

Additionally, or alternatively, one or more rear teeth 176 of the second jaw 142 may be greater in height than the rear tooth 164 of the first jaw 140. In the embodiment of FIG. 15A, the second jaw 142 is shown with two rear teeth 176 disposed at opposite sides of the grasping portion 148 and spaced apart by the jaw gap JG, which may extend to the distal end of the connection portion 146. In some embodiments of the second jaw 142, the rear teeth 176 may be the only pair of teeth that may be aligned with one another on opposite sides of the grasping portion 148. Additionally, or alternatively, at least one intermediate tooth 166 on one side of the grasping portion 148 may be arranged closer to the rear tooth 176 than another intermediate tooth 166 on the opposite side of the grasping portion 148 is closer to the rear tooth 176 on the opposite side.

With continued reference to the figures, and now with reference to FIG. 16A, one or more teeth of the first jaw 140 may overlap with one or more teeth of the second jaw 142. Additionally, or alternatively, one or more teeth of the first jaw 140 and the second jaw 142 may alternate as the outermost tooth of the microforceps assembly 100. FIG. 16A illustrates an exemplary embodiment where teeth from both jaws alternate as the outermost teeth of the microforceps assembly 100 such that each outermost tooth belongs to a different jaw.

Figure 17A:
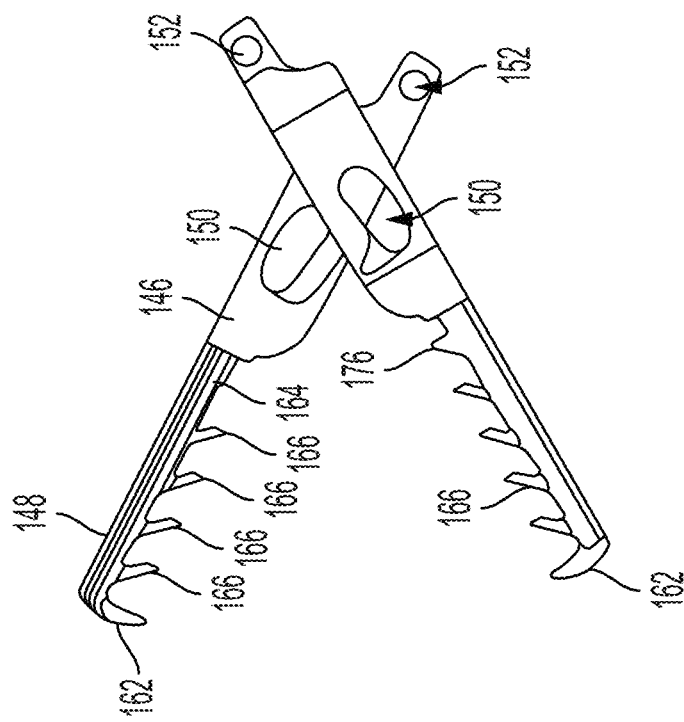
FIG. 17A illustrates a side view of another exemplary embodiment of a jaw in accordance with the disclosure provided herein.
Figure 17B:
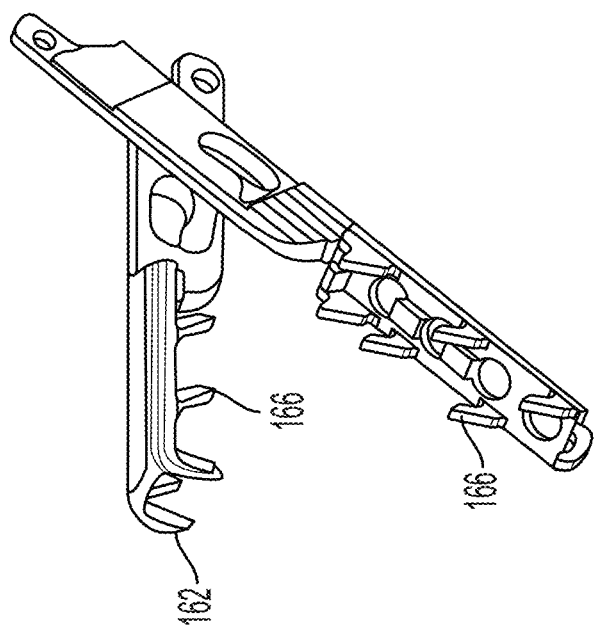
FIG. 17B illustrates a perspective view of the jaw of FIG. 17A.

With reference now to FIG. 17A and FIG. 17B, one or more teeth of the first jaw 140 and second jaw 142 may be primarily backwards angled (i.e., with minimal or no curvatures). This embodiments may be similar to the other embodiments of the jaws described herein in that a gap may be formed between the forward teeth of the first jaw 140 (and intermediate teeth 166 of both jaws) that may extend the length (or a portion of the length) of the grasping portion 148 (e.g., from the distal end of the grasping portion to a rear tooth at or near a proximal end of the grasping portion 148).

Figure 18:
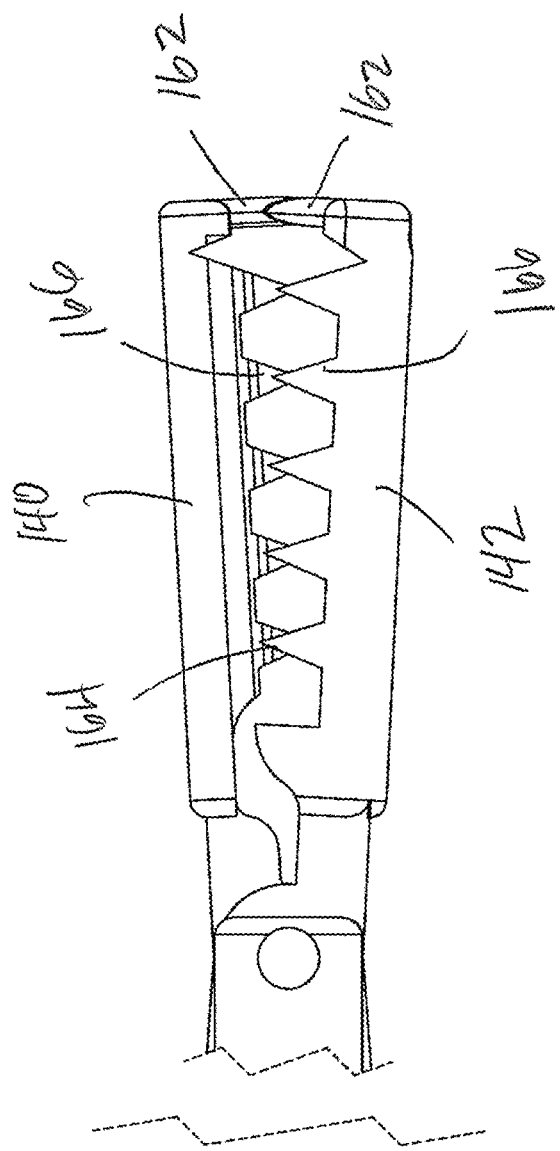
FIG. 18 illustrates a side view of another exemplary embodiment of a jaw in accordance with the disclosure provided herein.

With reference now to FIG. 18, one or more teeth in the first jaw 140 may be grooved or recessed (e.g., via machining) to allow for one or more tips of teeth in the second jaw 142 to be seated therein when the microforceps assembly 100 is in the closed position. It should be appreciated that only the intermediate teeth 166 of the first jaw 140 may be configured for corresponding teeth tips of the second jaw 142 to be seated therein. In some embodiments, one or more rear teeth 164 of the first jaw 140 may be recessed for seating any tips of corresponding rear teeth of the second jaw 142. Additionally, or alternatively, and as illustrated in FIG. 18, the tip portions within the seated (recessed) area near the distal end of the grasping portions 148 may be greater than the tip portions within the seated area near the proximal end of the grasping portions 148. It should be appreciated that providing an embodiment of the microforceps assembly 100 where one set of teeth sits inside another set of teeth may result in an improved closing and gripping force of the microforceps assembly 100.

It is to be understood that the detailed description is intended to be illustrative, and not limiting to the embodiments described. Other embodiments will be apparent to those of skill in the art upon reading and understanding the above description. Moreover, in some instances, elements described with one embodiment may be readily adapted for use with other embodiments. Therefore, the methods and systems described herein are not limited to the specific details, the representative embodiments, or the illustrative examples shown and described. Accordingly, departures may be made from such details without departing from the spirit or scope of the general aspects of the present disclosure.

Additionally, the components and materials described hereinafter as making up the various embodiments are intended to be illustrative and not restrictive. It should be appreciated that many suitable components and materials that would perform the same or a similar function as the materials described herein are intended to be embraced within the scope of embodiments of the present disclosure.

We claim:

1. An endoscopy device comprising:
   a fork defining a guide channel and including a pair of fork pins at a distal end of the fork within the guide channel;
   a pair of control arms pivotally mounted about the fork at a proximal end of the guide channel; and
   a pair of jaws movable between a closed position and open position,
      wherein each jaw includes a grasping portion having a plurality of teeth and a connection portion, wherein the grasping portion includes at least a front tooth formed at a distal end of the grasping portion and a plurality of rear teeth formed between the front tooth and a proximal end of the grasping portion;
      wherein the connection portion includes a first opening at a distal end of the connection portion and a second opening at a proximal end of the connection portion, wherein the first opening is elongated and the pair of jaws are pivotally mounted directly to the pair of fork pins at a distal end of the guide channel via the first opening, wherein the pair of fork pins are offset from one another within the guide channel and wherein each jaw is pivotally mounted to one of the pair of control arms via the second opening.

2. The endoscopy device of claim 1, wherein one or more of the rear teeth are angled towards the proximal end of the grasping portion.

3. The endoscopy device of claim 1, wherein one or more of the rear teeth are backwards curved towards the proximal end of the grasping portion.

4. The endoscopy device of claim 1, wherein one or more of the rear teeth of one jaw includes a recessed tip portion having a shape corresponding to an opposing tip of one or more rear teeth of the other jaw.

5. The endoscopy device of claim 1, wherein the rear teeth of each jaw are offset with respect to each neighboring rear tooth along edges of the grasping portion.

6. The endoscopy device of claim 5, wherein the offset rear teeth of each jaw are positioned along the edges of the grasping portion such that the rear teeth of both jaws overlap when the jaws are in the closed position.

7. The endoscopy device of claim 5, wherein the offset rear teeth of each jaw are positioned along the edges of the grasping portion such that the rear teeth of both jaws alternate as the outermost tooth along the edges of the grasping when the jaws are in the closed position.

8. The endoscopy device of claim 1, wherein at least one jaw includes a fenestration extending through a thickness of the grasping portion.

9. The microforceps assembly of claim 1 further comprising:
   a pusher disposed within the guide channel, and wherein each control arm is pivotally mounted at one end of the pusher for closing and opening the jaws via a movement of the pusher.

* * * * *